United States Patent [19]
Maeda et al.

[11] Patent Number: 5,681,265
[45] Date of Patent: Oct. 28, 1997

[54] CYLINDRICAL ANAL RETRACTOR

[75] Inventors: Koutarou Maeda, Urawa; Takashi Sugawara, Tokyo, both of Japan

[73] Assignee: Yufu Seiki Co., Ltd., Japan

[21] Appl. No.: 516,044

[22] Filed: Aug. 17, 1995

[30] Foreign Application Priority Data

Sep. 2, 1994 [JP] Japan .................................. 6-232527
Sep. 2, 1994 [JP] Japan .................................. 6-232528

[51] Int. Cl.$^6$ .................................................. A61B 11/02
[52] U.S. Cl. ...................... 600/219; 600/214; 600/221; 600/224; 600/215; 606/197; 606/198
[58] Field of Search ................................ 600/114, 201, 600/208, 210, 214, 215, 216, 219, 220, 221, 224, 225, 235; 606/197, 198

[56] References Cited

U.S. PATENT DOCUMENTS

| | | | |
|---|---|---|---|
| 424,140 | 3/1890 | Shilford | 600/219 |
| 832,201 | 10/1906 | Kistler | 606/198 X |
| 1,244,751 | 10/1917 | McCleary | 606/197 |
| 4,690,132 | 9/1987 | Bayer et al. | 600/219 |
| 5,377,667 | 1/1995 | Patton et al. | 600/214 X |
| 5,509,893 | 4/1996 | Pracas | 600/214 X |

*Primary Examiner*—Beverly M. Flanagan
*Attorney, Agent, or Firm*—Price, Heneveld, Cooper, DeWitt & Litton

[57] ABSTRACT

A cylindrical anal retractor for examining the inside of an anus of a living body including an inserting valve portion inside of which a substantially circular-shaped opening is formed, a handle which serves to dilate the opening by gripping it, and an auxiliary appliance for making the insertion of the inserting valve portion into the anus smooth; the trivalve inserting portion has three plate-like members, which are curved inside, and two of the members are connected to the handle so as to be rotatable about axes extended in an inserting direction of the inserting valve portion. In the anal retractor according to the present invention, therefore, the pain which is given to the patient when the anal retractor is inserted into his or her anus is remarkably reduced.

18 Claims, 6 Drawing Sheets

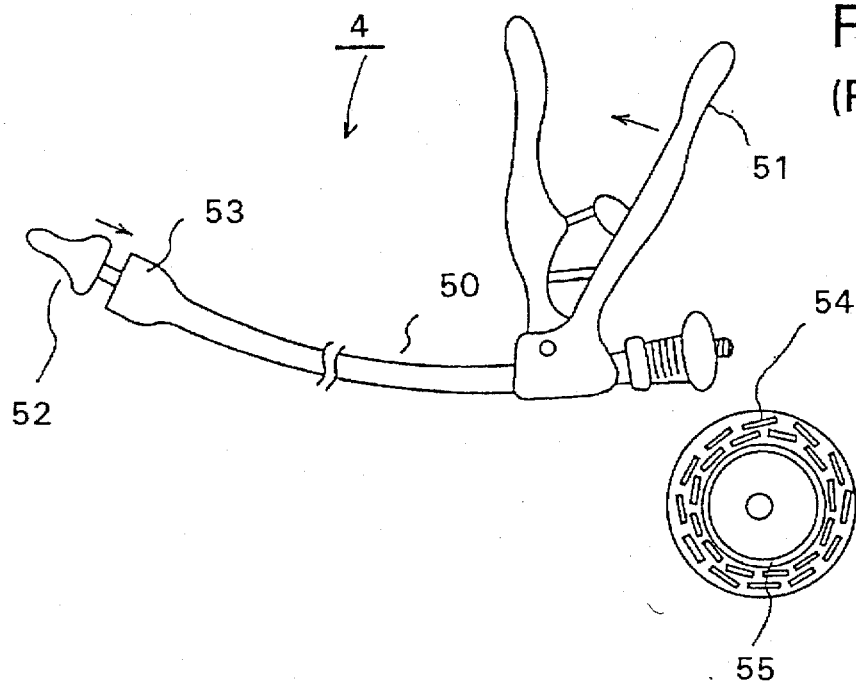
Fig. 3A (PRIOR ART)
Fig. 3B (PRIOR ART)
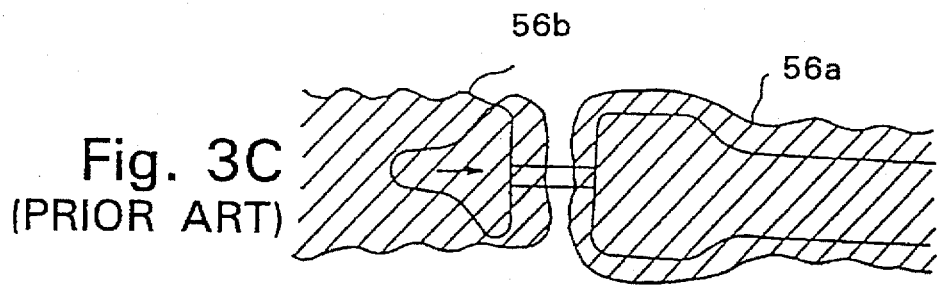
Fig. 3C (PRIOR ART)
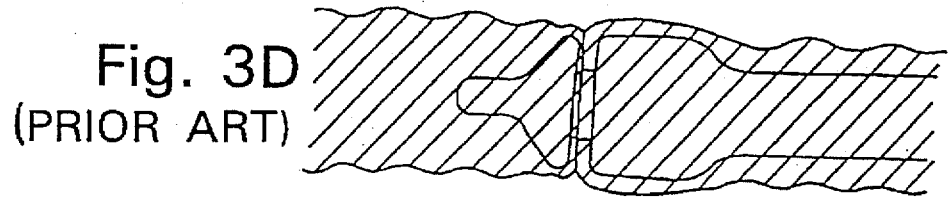
Fig. 3D (PRIOR ART)
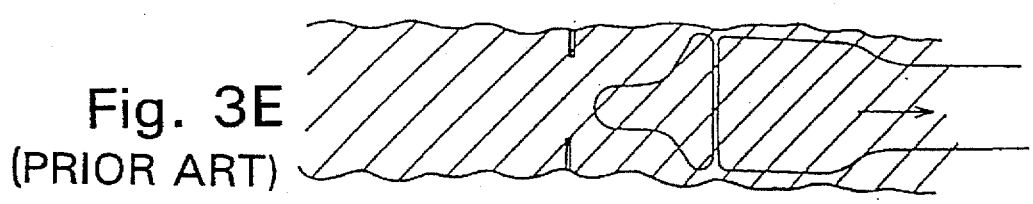
Fig. 3E (PRIOR ART)

Fig. 5A
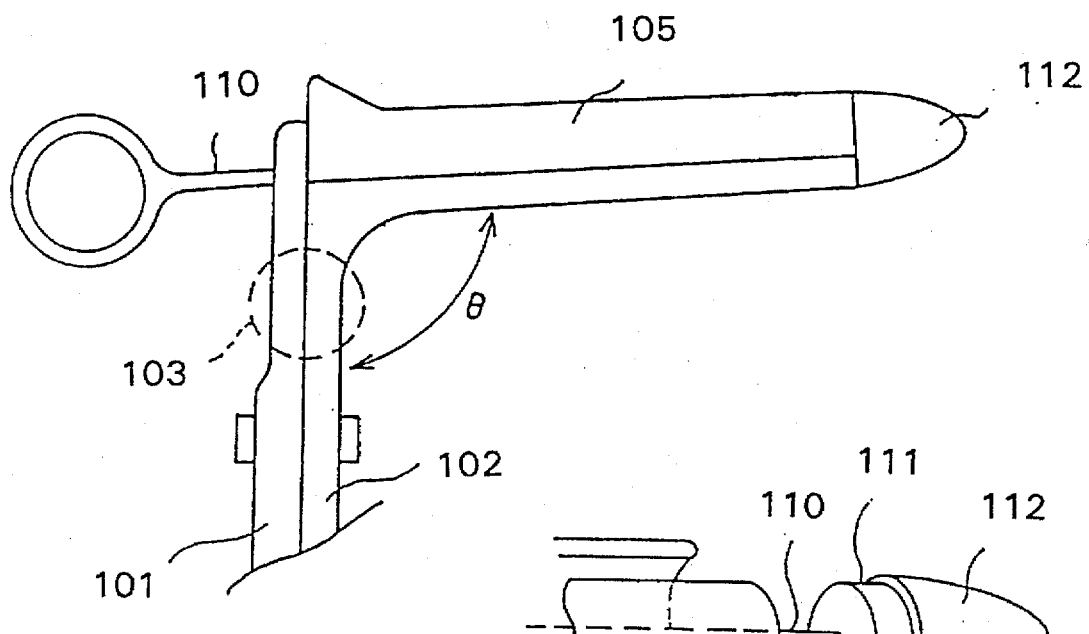
Fig. 5B
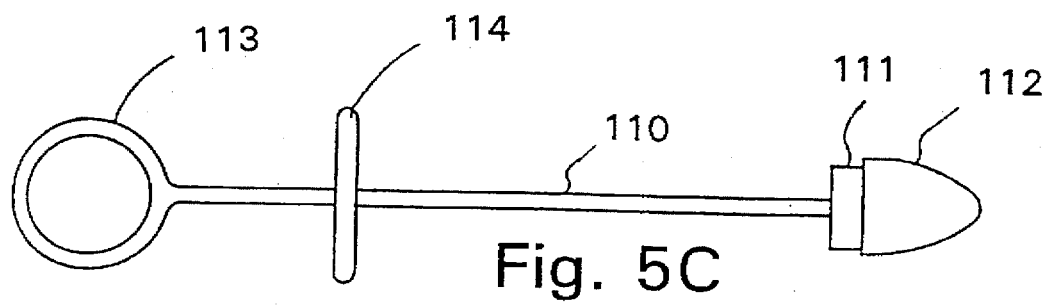
Fig. 5C

CYLINDRICAL ANAL RETRACTOR

BACKGROUND OF THE INVENTION

1. Field of the Invention

The present invention relates to a cylindrical anal retractor, more particularly, to a trivalve cylindrical anal retractor which is used in an operation or as assistance in an operation, upon the inside of an anus or rectum of a living body.

2. Prior Art

As is well known, an anal retractor is used to examine the inside of an anus and/or rectum of a living body by inserting the distal end portion thereof into the anus and/or rectum. The anal retractor is also used as an auxiliary appliance for inserting medical appliances such as forceps and fiber scopes into the anus or rectum in order to examine, wash, or treat the inside wall thereof. Recently, such an anal retractor is frequently used to perform an operation with the inside wall thereof. Such operations are advantageous to patients because the operation can be performed without a laparotomy.

On the other hand, an inosculating device is often used to inosculate damaged canals. Such a device is inserted into the damaged canals via the anus in accordance with a portion to be inosculated, then operated to inosculate them with each other. When inserting the inosculating device into the anus, the operator hitherto dilated the anus with his or her fingers. However, it is difficult to insert the inosculating device into the anus without great pain to the patients and also is difficult to get a good surgical field with the previous device. In order to make the insertion of the inosculating device easy and safe and to get a better surgical field, the anal retractor is recently used as an auxiliary appliance for inserting the inosculating device into a cavity via an anus.

FIG. 1(A) is a perspective view showing the construction of a conventional cylindrical examination anal retractor. The conventional anal retractor comprises a cylindrical anal retractor body 1 and an auxiliary appliance 2, which allows the anal retractor to be inserted into the anus smoothly; the cylindrical anal retractor body 1 consists of a cylindrical inserting portion 10 and a handle 11. On a distal end portion of the auxiliary appliance 2, a bullet shaped insertion head 20 is provided, and on a proximal end portion thereof are arranged a finger hook ring 21 and a holder 22.

The conventional cylindrical examination anal retractor is used under the condition illustrated in FIG. 1(B). That is to say, the auxiliary appliance 2 is inserted into the cylindrical inserting portion 10 of the anal retractor body 1 and fixed therein with the aid of the holder 22. Since the cylinder 10 has a tapered shape, whose posterior side is larger than the anterior side, the auxiliary appliance 2 can be easily secured in the inserting portion 10 with the aid of the plate-like holder 22. After the auxiliary appliance 2 is mounted and secured in the inserting portion 10 in this manner, the inserting portion 10 of the anal retractor is inserted into the anus of a patient in a direction as shown by the arrow A. After inserting portion 10 is inserted a predetermined depth into the anus; an operator pulls the auxiliary appliance 2 from the anal retractor in a counter direction as shown by the arrow B to remove it, leaving the cylindrical anal retractor body in the anus. The operator can easily remove the appliance 2 by hooking his or her finger on the ring 21. The anal retractor is inserted into the anus of a patient in this manner. The inside of the anus or rectum of the patient is exposed via an opening of the anal retractor and the operator can examine the exposed inside using a naked eye; and then the operator can provide the suitable treatment such as a washing on the affected part of the anus or rectum or perform an operation.

However, as clear from FIG. 1, such a conventional anal retractor has only one opening at the distal end of the cylindrical inserting portion to expose the inside of the cavity. Since the entire wall of the anus or rectum cannot be exposed via this opening, the operator cannot fully examine the inside of the anal wall and it is difficult to perform an operation with such a small field of view. Further, in order to examine the inside fully and give a suitable treatment on the affected part, the operator has to move the anal retractor in the cavity; but, such a movement of the anal retractor gives great pain to the patient.

Furthermore, when the anal retractor is inserted into the cavity, the auxiliary appliance 2 should be inserted into the cylindrical anal retractor body 10, which is formed as a united body, and the bullet-shaped top portion 20 provided at the distal end of the auxiliary appliance 2 is protruded from the opening of the cylindrical body 10. Therefore, a step 3 is formed at the connected portion of the opening of the cylindrical body 10 and the outer surface of the top portion 20 of the auxiliary appliance 2, as shown in FIG. 1(C). This step gives greater pain to the patient when the anal retractor is inserted into his or her anus.

FIG. 2 is a schematic view showing the construction of a conventional trivalve anal retractor, which has been developed in order to obtain a wider field of view and reduce the pain to the patient when the anal retractor is inserted into his or her anus or the anal retractor is moved inside of his or her cavity. In FIG. 2(A), which is a plan view of the anal retractor, the numerical reference 41 represents a handle, 42 a slidable stay, 43 a gauge screw, 44 a spring and the numerical reference 45 represents an inserting valve portion. FIGS. 2(B) and 2(C) are side views of the inserting valve portion 45, which is arranged to be able to open. FIG. 2(B) shows a condition where the valves are closed together and FIG. 2(C) depicts a condition where the valves are separated from each other to obtain an opening inside of the inserting valve portion 45. The numerical references 45a to 45c, respectively, represent valves, 46 an opening formed there inside and 47 shows a round inside wall of each valve. As shown in FIG. 2(B), the distal end portion of the valves 45 is arranged to form a bullet shape when the valves are closed together, so that the anal retractor can be inserted into the anus without giving much pain to the patient.

In the thus constructed trivalve anal retractor, when no force is given to the handle 41, the valves 45a to 45c are closed together by the energy of the spring 44; but when gripping the handle 41, both the upper left and the upper right valves 45a and 45b are opened in left and right directions. At the same time, the slidable stay 42 is moved to a rear direction; and in accordance to the movement of the slidable stay 42, another valve 45c is moved to a lower direction shown in FIG. 2(B) to form an opening 46 inside of the valve portion 45.

The trivalve examination anal retractor is inserted into the anus until it reaches a predetermined depth under the condition that the valves 45 are closed together; and then the valves 45 are opened by gripping the handle 41 to form an opening 46 inside of the valves 45 as shown in FIG. 4(C). The operator visually examines the inside of the anus via the opening 46 and gives a suitable treatment, such as washing, to the affected part of the patient. In the anal retractor shown in FIG. 2, it is possible to obtain a wider field of view in comparison with the retractor shown in FIG. 1. However, the field of view thereof is not enough to fully examine the inside of the anus or perform an operation.

In addition to the above, in the conventional trivalve anal retractor, the valve portion 45 is connected to the handle 41 so as to form a right angle, as shown in FIG. 2(B). Therefore, the anal retractor has a drawback that it is difficult for the operator to control the anal retractor easily after the anal retractor is inserted into the anus.

The anal retractor has another drawback namely that an ideal circular-shaped opening cannot be obtained at the distal end thereof. In the trivalve anal retractor, it is desired that each valve opens outside in an even manner. However, in the conventional anal retractor, the upper left and the upper right side valves 45a and 45b are fixed to the ends of the handle 41, respectively; therefore, these vales are opened to the perspective lower directions, respectively, as shown by the arrows c and d in FIG. 4(B). Furthermore, the valves are designed to form a bullet shaped top when the valves are closed together, in order to make the insertion thereof into the anus easy, taking the pain given to the patient into consideration. Therefore, each of the valve has a round surface, which is curved inside of the inserting portion. Thus, when the valves 45 are opened after the anal retractor is inserted into the anus, the round portions 47 of the valves protrude inside the opening 46, so that the actual circular-shaped opening cannot be obtained in the conventional trivalve anal retractor. It should be noted that the round shaped valves prevent a full examination of the inside of anus and also hinders an operation.

FIG. 3 shows the construction of a conventional inosculating device for inosculating damaged alimentary canals. In FIG. 3(A), the numerical reference 4 represents an inoculator, 50 an inserting portion thereof, 51 a handle, 52 a first inosculating section and 53 represents a second inosculating section. FIG. 3(B) is a cross-sectional view of the first inosculating section 52. As shown in FIG. 3(B), on the outer circumference of the first inosculating section 52, a plurality of clips 54 are arranged; and in an inner circumference thereof, there is embedded a cutter for cutting out the damaged alimentary canals. As stated in the above, such an inosculating device is inserted into the damaged alimentary canals via the anus and used to inosculate them to each other as like a stapler.

The inosculation is conducted in such a manner that the inserting portion 50 is inserted into the damaged canals via the anus of the patient until the first inosculating section 52 disposed at a distal end of the inserting portion 50 is exposed from one of the separated (damaged) alimentary canals 56a; then the first inosculating section 52 is further pushed out until the first inosculating section 52 is covered with the other separated (damaged) alimentary canal 56b, as shown in FIG. 3(C). Then the handle 51 is gripped or closed to fit the first inosculating section 52 with the second inosculating section 53. By this gripping operation, the separated (damaged) alimentary canals 56a and 56b are inosculated to each other with the aid of the clips arranged in the outer circumference of the first inosculating portion 52. At the same time, the cutter 55 operates to cut out the damaged part of the canals. After the inosculation is finished, the inoculator 4 is taken off from the cavity via the anus, as shown in FIG. 4(E).

Hitherto, when such inosculation was conducted, the inoculator 4 was inserted into the anus of the patient, directly. The operator open the anus of the patient with his or her fingers and therefore, sometimes the anus was hurt and caused the patient great pain. In addition to this, since an anus generally has a contractility, the inoculator 4 was inserted into the anus with great attention by the operator and with great force to push it into the anus, so it was difficult for the operator to insert the device into the cavity via the anus and use the device smoothly.

The inosculation of the damaged alimentary canals was conducted in such a condition that the canals to be inosculated to each other were kept dilated by the inosculating device 4. Therefore, the distal end of the inserting portion 50 of the device was designed to be larger than the diameter of the canals to be inosculated. If the device having such large diameter of the inserting portion is directly inserted into the anus of the patient, not only the insertion is difficult but also the patient experiences great pain.

Moreover, since great force is necessary to insert the device into the anus or remove it therefrom, it is required that the other operator keep the anus of the patient open with the aid of an anus opening appliance, during which the inosculating device is inserted into the anus or taken therefrom. Therefore, at least two operators are necessary to conduct the inosculation of the alimentary canals when the conventional device is used.

SUMMARY OF THE INVENTION

One purpose of the present invention is to provide a cylindrical anal retractor having a large field of view, which is easily used by an operator, and can be inserted into the patient's anus without great discomfort to the patient. In order to carry out the invention, the cylindrical anal retractor according to the present invention has a construction which allows the anal retractor to be smoothly inserted into the anus, and after the insertion the anus can be dilated enough to obtain a larger field of view without giving pain to the patient. The valves which form the inserting portion of the retractor have thin and curved plate-like shapes so that an excellent circular-shaped view field can be obtained when the valves open in the anus. Further, a part of the valve portion is arranged to be rotatable about axes extended in an inserting direction of the valve portion, so that no exceeding tension is given to the anus of the resulting patient and the pain is reduced when the valve portions are opened after the insertion. Furthermore, the inserting portion of the anal retractor is connected to the handle with an angle of 90 degrees or more to improve the controllability of the anal retractor; and the outer surface of the inserting portion of the anal retractor is designed to be smooth by providing a step on an outer surface of the distal top portion of the auxiliary appliance of the anal retractor, so that the anal retractor can be inserted into the anus smoothly.

The second purpose of the present invention is to provide an inosculating device having an anus dilator. By the inosculating device according to the present invention, the anus dilator is inserted into the anus first, and then the inoculator is inserted into the alimentary canal via the dilated anus using the dilator as a guide, and thereafter the anus dilator is removed. Therefore, it becomes easy to insert and remove the inosculating device into and from the canal via the anus and the pain to the patient during the inosculation of the alimentary canals is much reduced.

BRIEF DESCRIPTION OF THE DRAWINGS

FIG. 3 is a schematic view depicting a construction of a conventional inosculating device for inosculating alimentary canals;

FIG. 5 is a schematic view showing a condition that an auxiliary appliance is mounted in the trivalve examination anal retractor according to the present invention and;

DETAILED EXPLANATION OF THE PREFERRED EMBODIMENTS

The preferred embodiments of the cylindrical anal retractors according to the present invention are explained below.

Figure 4A:
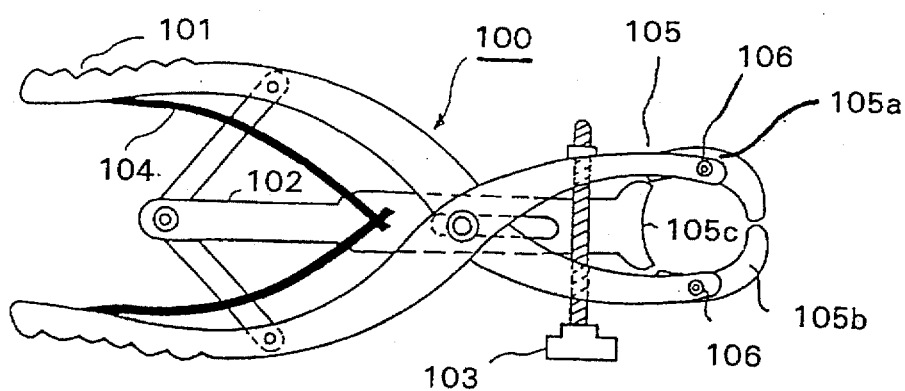
FIG. 4 is a schematic view representing a construction of a trivalve examination anal retractor according to the present invention.
Figure 4B:
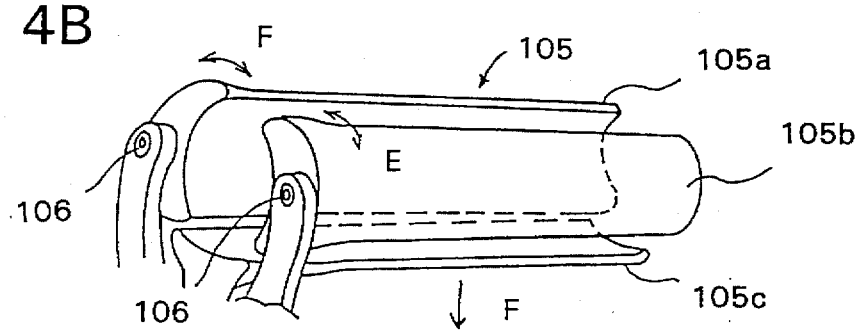

FIG. 4(A) is a plan view showing a construction of a trivalve examination cylindrical anal retractor according to one embodiment of the invention; and FIG. 4(B) is a perspective view depicting an inserting portion of said anal retractor in an enlarged scale. In FIG. 4, the numerical reference 100 represents an anal retractor body, 101 a handle, 102 a slidable stay, 103 a gauge screw, 104 a spring, 105 an inserting valve portion, and the numerical references 105a to 105c represent valves, respectively. The valves 105a and 105b are secured to an end portion of the handle 101 so as to be rotatable about axes extended in an inserting direction of the anal retractor 100. The numerical reference 106 represents pins for securing the valves 105a and 105b to the handle 101 in a rotatable manner. These pins serve as the rotating axes of these valves 105a and 05b. On the other hand, another valve 105c is fixed to an end portion of the slidable stay 102. Therefore, when the operator grips the handle 101, these valves 105a, 105b and 105c open outside, and are separated from each other, so that the valve portion 105 opens outside to form an opening inside thereof. As shown in FIG. 4(B), when the valve portion 105 opens outside, the valves 105a and 105b are separated from each other, keeping their condition to be freely rotatable in directions shown by the arrows E and F. In this manner, the trivalve examination cylindrical anal retractor 100 according to the present invention is designed such that the valve portion 105 can be dilated and some parts of the cylindrical inserting portion (valve portion) 105 are rotatable with respect to the handle 101. Therefore, when the inserting valve portion 105 is inserted in the anus, no excessive tension it given against the inside wall of the anus.

In the anal retractor according to the present invention, a cylindrical body is constituted of the valve portion 105: and each valve comprises a loosely curved plate-like member. Thus a circular opening is obtained at the distal portion of the inserting valve portion 105. That is to say, the operator can obtain a wide view field with the anal retractor.

The anal retractor 100 is inserted into a cavity, such as an anus, with the aid of an auxiliary appliance 110 as like the conventional cylindrical examination anal retractor. FIG. 5(A) is a side view showing a condition when the auxiliary appliance 110 is inserted into the cylindrical body(inserting valve portion) 105 of the anal retractor 100. The inserting valve portion 105 of the anal retractor 100 is inserted into an anus of a patient under the condition shown in FIG. 5(A). According to the present invention, the inserting valve portion 105, which forms the cylindrical body, is fixed to the handle 101 so as to form an angle α, which is 90 degrees or more, between the valve portion 105 of the anal retractor and the handle 101. Therefore, the operator can easily handle the anal retractor when the anal retractor is inserted in or removed from the cavity via the anus.

Figure 1A:
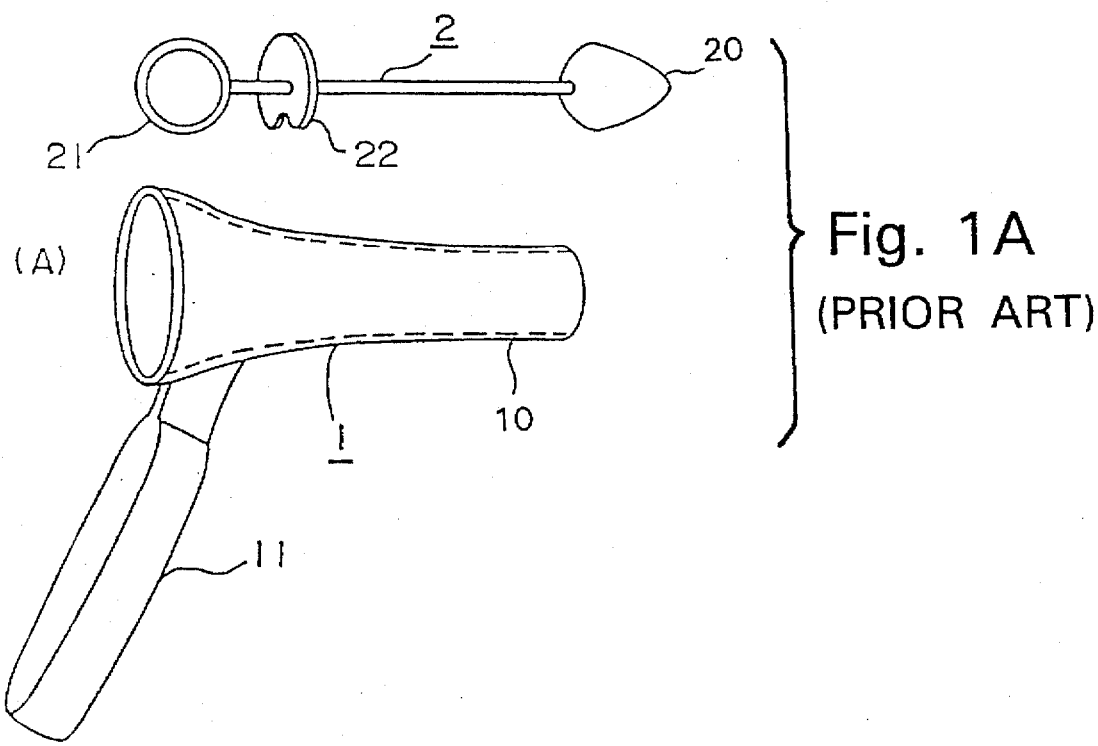
FIG. 1 is a schematic view showing a construction of a conventional cylindrical examination anal retractor.
Figure 1B:
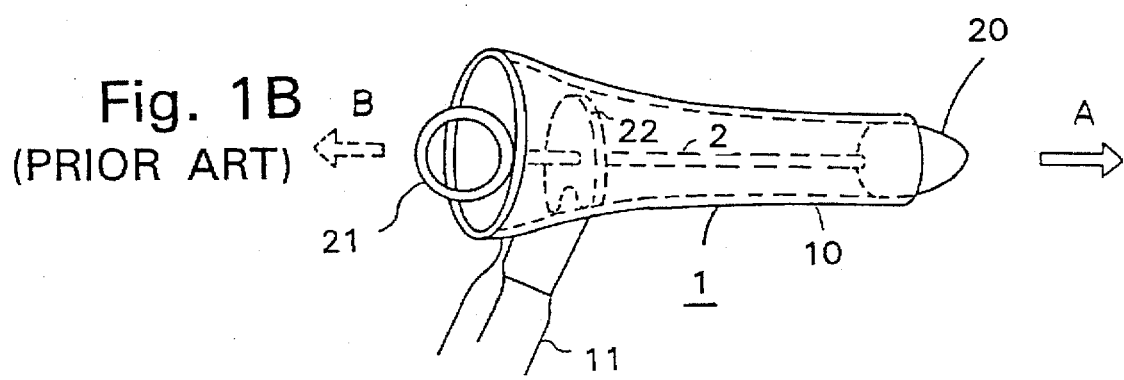
Figure 1C:
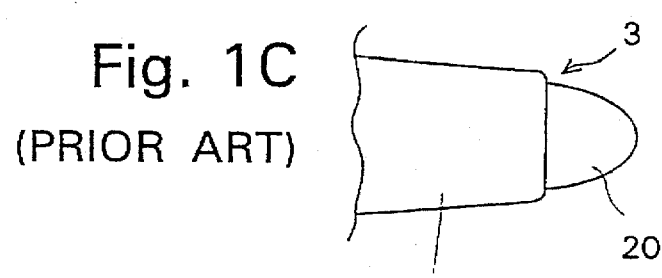
Figure 2A:
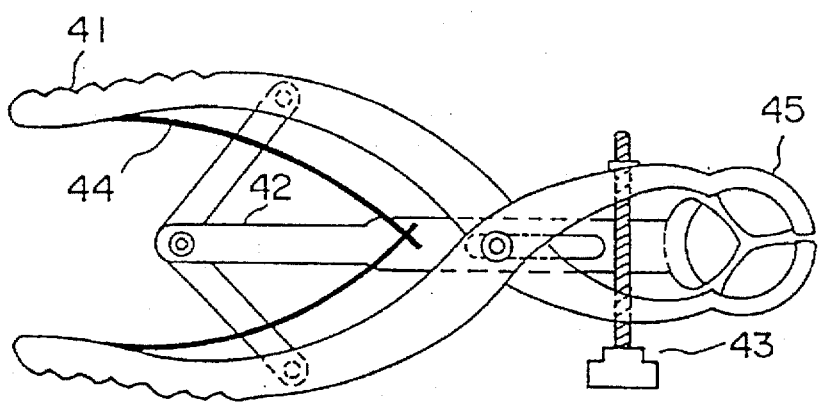
FIG. 2 is a schematic view illustrating a construction of a conventional trivalve examination anal retractor.
Figure 2B:
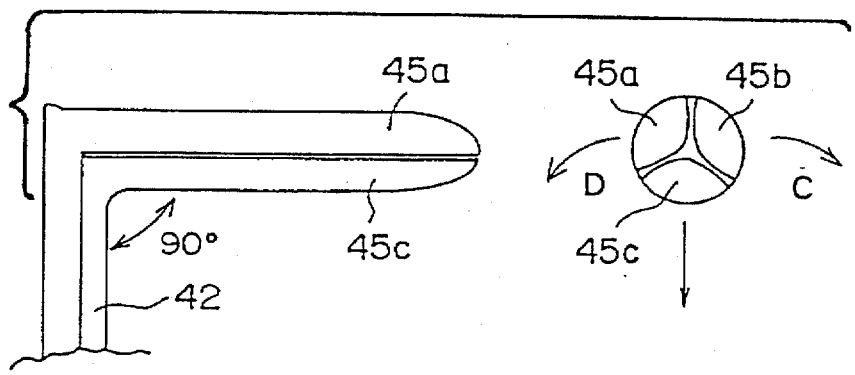
Figure 2C:
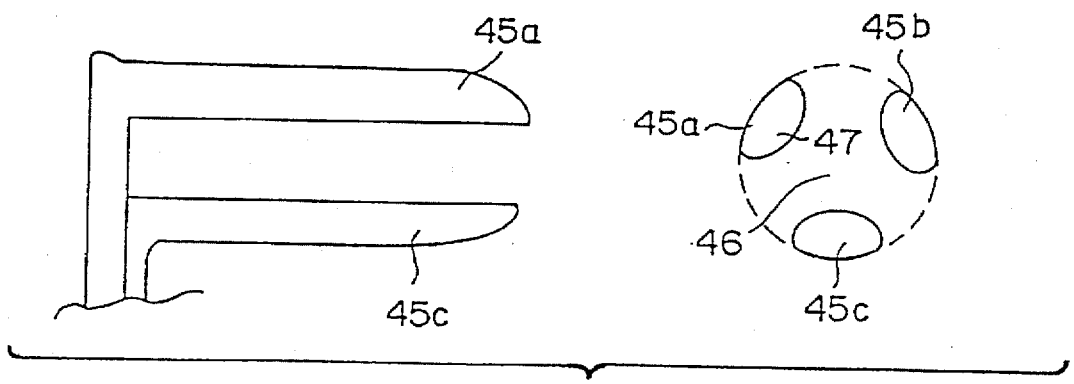

The auxiliary appliance 110 has the same construction as that of the conventional one shown in FIG. 1, with the exception of the construction of a distal top portion 112 thereof. It should be noted that the explanation for the parts than the distal top portion 112 is therefore omitted here. In the auxiliary appliance 110 used in the anal retractor according to the invention, around an outer surface of the bullet shaped distal top portion 112, is provided a step 111 as shown in FIG. 5(B). Therefore, when the auxiliary appliance 110 is mounted into the cylindrical body of the anal retractor 100, the step 111 is suitably coupled with the opening of the cylindrical body 105. Therefore, the connecting portion between the distal top portion 112 of the auxiliary appliance 110 and the opening of the cylindrical body 105 is smooth, so that it is easier to insert the anal retractor into an anus and pain reduces of the patient when the anal retractor is inserted.

While the anal retractor, in which the auxiliary appliance 110 is mounted, is inserted into the anus to a predetermined depth the valves 105 are closed. Once of the desired depth, the operator grips the handle 101 a little to open the valves 105 in order to remove the auxiliary appliance 110 from the cylindrical body of the anal retractor 100. Since the step 111 is provided on the distal top portion 112 of the auxiliary appliance 110, the appliance 110 cannot be removed therefrom without opening the valves 105.

After taking off the auxiliary appliance 110 from the cylindrical body, the operator grips the handle 101 again to open the valves 105 much more to obtain a circular view field having a desired dimension at the distal end of the cylindrical body. In order to keep the dimension of the view field, the opening degree of the handle is fixed with the aid of the gauge screw 103. It should be noted that other latch mechanisms may be used instead of the gauge screw 103. In the anal retractor according to the present invention, since the valves 105a, 105b and 105c are designed to be plate-like members which are curved inside, respectively, it is possible to obtain a circular and wide view field when the valves are open. Therefore, the operator can conduct a visual examination, and provide suitable treatment easily through the circular-shaped opening. Further, the circular and wide opening creates access in an operation on the anus or rectum.

When the valves 105 are open, each of the valves 105a to 105c is strongly urged against the inside wall of the anus or rectum, and thus the patient gets pain. However, according to the present invention, since the upper side valves 105a and 105b are arranged to be rotatable about axes extended in an inserting direction of the anal retractor, the tension against the anus wall is remarkably reduced.

Figure 6A:
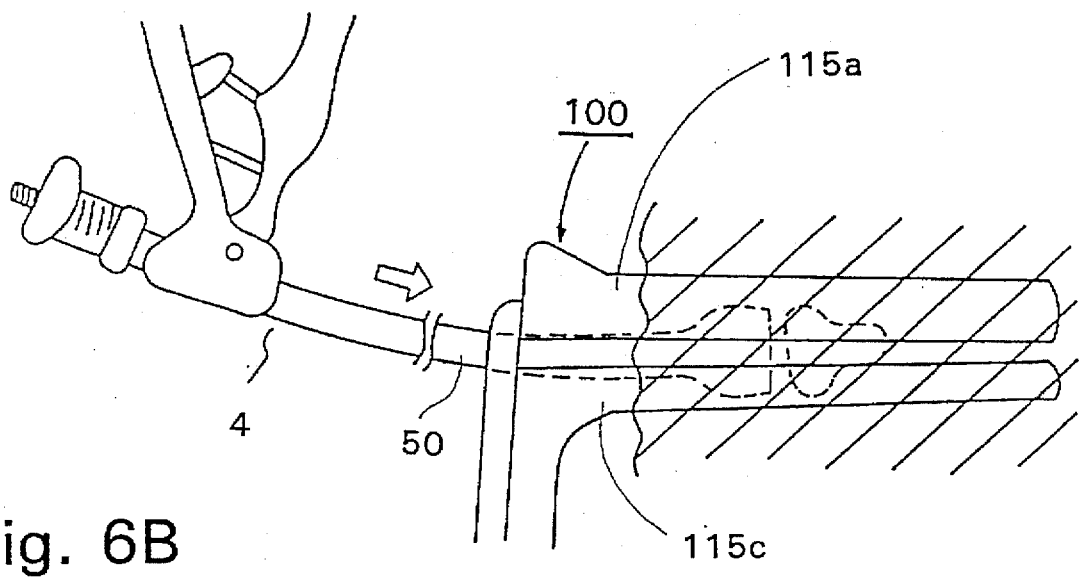
FIG. 6 is a schematic view illustrating a condition that the inosculating device according to the present invention is used.
Figure 6B:
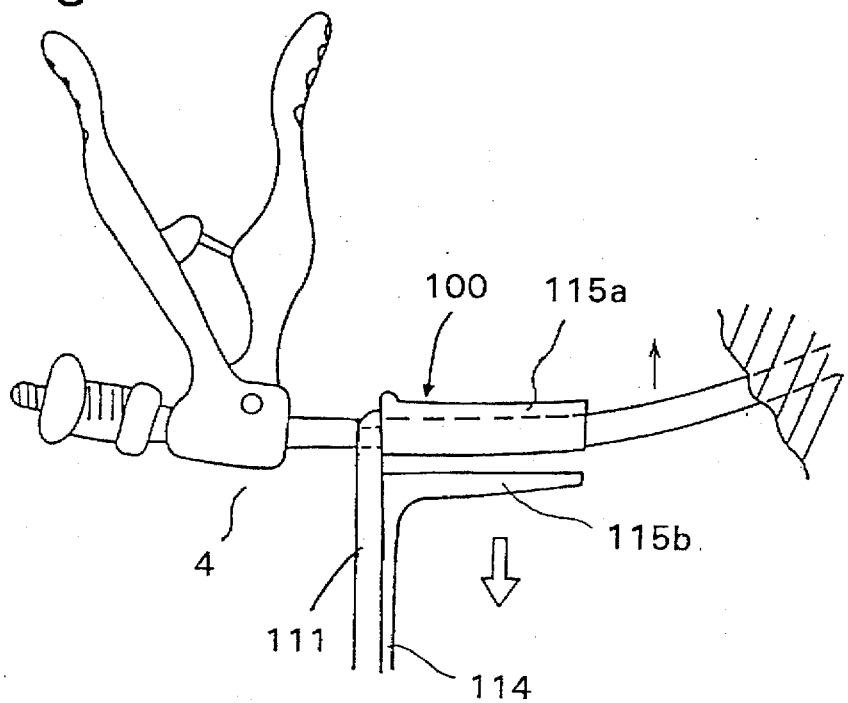

FIG. 6 shows another embodiment of the invention and including an inosculating device for inosculating alimentary canals. The inosculating device comprises an inoculator 4 and an anus dilator 100 which is suitably used as a guide for the inoculator 4. The anus dilator 100 has almost the same construction as that of the anal retractor according to the prior embodiment of which is shown in FIG. 4; but the gauge screw is not provided therein. Further, it should be noted that the inoculator 4 has the same construction as the conventional device illustrated in FIG. 3. Therefore, the same numerical references in FIGS. 3 and 4 are given to the same elements of the anus dilator 100 and the inoculator 4 in FIG. 6 and the explanations for the same elements are omitted here. It should be noted, however, that the anus dilator 100 should have a sufficient diameter, such that the first and second inosculating sections 52 and 53 of the inosculating device may easily be inserted.

According to this embodiment of the inosculating device the inoculator is inserted into a cavity with the aid of the dilator 100. Therefore, the inoculator can be inserted into the cavity very easily and smoothly, because the dilator acts as a guide.

The function of the inosculating device will be explained below. First, the auxiliary appliance 110 is mounted in the anus dilator 100 as explained previously. Since the step 111 is provided on the outer circumference of the distal top portion 112 of the auxiliary appliance 110, the connecting portion of the dilator 100 and the auxiliary appliance 110 is smooth, so that the dilator 100 can be easily inserted into the anus and the pain for the patient is reduced.

Next, the anus dilator 100, with the auxiliary appliance 110, is inserted into the anus of the patient. After inserting the dilator 100 to a predetermined depth, the operator grips the handle 101 to open the valves 105; then the auxiliary appliance 110 is removed from the dilator 100, leaving the dilator 100 in the anus. Then, the inserting portion 50 of the inoculator 4 is inserted into the alimentary canal via the anus using the dilator 100 as a guide.

In this way, a bullet shaped distal top portion of the auxiliary appliance 110 according to the second invention, which is connected to the dilator forming a smooth outer surface, is inserted into the anus first and the anus is dilated a little by this insertion. Thereafter, the inoculator 4, which has a larger diameter on its inserting portion, is inserted, keeping the dilated condition of the anus by the dilator 100. Therefore, the operator can easily insert the inoculator into a desired portion of a cavity and the great pain, which the patient would have experienced if the conventional inosculating device was inserted into the anus directly, can be remarkably reduced.

Further, leaving the inserting portion 50 of the inoculator 4 in the anus and the portion of the alimentary canal to be treated, the anus dilator 100 can be removed from the anus. After the dilator 100 is completely removed from the anus, the valves 105 of the dilator 100 are opened by gripping the handle 101 such that the dilator can be separated from the inoculator 4. As stated above, since the valves 105a and 105b are arranged to be rotatable about axes extended in an inserting direction of the dilator, the dilator 100 can be easily separated from the inoculator 4, keeping the condition that the inoculator 4 is still inserted in the anus and the alimentary canal.

According to the inosculating device of this invention, the dilating operation of the anus and the insertion of the inosculating device into the alimentary canal can be easily conducted by only one operator. That is to say, the operator dilates the anus of a patient with one of his or her hands, while the same operator can insert the inoculator with the other hand very easily.

After the inosculating operation is finished, the inosculating device 4 is removed from the cavity via the anus with the aid of the anus dilator 100 in the reverse order of the above-explained operation. In this case, the removal of the inoculator can also easily be carried out and the pain experienced by the patient is extremely reduced the same as in the case of insertion.

The present invention is not limited to the above embodiments. For instance, in the above mentioned embodiments, the inserting portion of the anal retractor (anus dilator) comprises three plate-like valve members. However, the number of valve members is not limited to three, but two or four or more valve members may be used unless the valve members function in the same manner. Further, the anus dilator according to this invention may be used as a guide when forceps or fiber scopes are inserted into the anus or the alimentary canal via the anus.

What is claimed is:

1. A cylindrical anal retractor system, comprising:

a cylindrical body having a plurality of plate-like members, each of which are curved, and arranged to form a substantially circular opening;

a handle means, having grip portions and a slidable stay connected to said plurality of said plate-like members for dilating said circular opening of the cylindrical body keeping the substantially circular shape thereof;

a holding means, operably coupled to said handle means, for maintaining the dilated condition of said cylindrical body;

a connecting means for connecting said plate-like members and said handle means; and an auxiliary appliance having a bullet shaped top portion, which is suitably mounted in the cylindrical body to protrude from a distal end of said circular opening of the cylindrical body;

wherein at least two of said plate-like members are connected to said grip portions of said handle means, respectively, so as to be rotatable about axes extended in a longitudinal direction of said cylindrical body and another one of the members is connected to said slidable stay of said handle means.

2. A cylindrical anal retractor according to claim 1, wherein: said handle means is connected to said cylindrical body so as to form an angle of 90 degrees or more therebetween.

3. A cylindrical anal retractor according to claim 1, wherein: said top portion of said auxiliary appliance comprises a step around an outer surface thereof, so that when said auxiliary appliance is inserted into the cylindrical body and protruded from said opening of the body, a smooth connection is obtained between the top portion and the opening of the cylindrical body.

4. An inosculating system for inosculating alimentary canals comprising:

a cylindrical body having a plurality of plate-like members, each of which are curved, and arranged to form a substantially circular opening;

a handle having grip portions and a slidable stay connected to said plate-like members;

a pin interconnecting said plate-like members to said handle; and an auxiliary appliance having a bullet shaped top portion, which is suitably mounted in the cylindrical body and arranged to protrude from a distal end of said circular opening of the cylindrical body; and an inosculating means having an inserting portion, a clipping mechanism disposed at a distal end of said inserting portion, and an operating portion disposed at a proximal end of said inserting portion, whereby damaged alimentary canals are inosculated with each other by inserting said inserting portion into said canals and operating said portion at a proximal end of the inserting portion;

wherein at least two of said plate-like members are connected to said handle so as to be rotatable about axes extending in a longitudinal direction of said cylindrical body, and another one of said plate-like members is connected to said slidable stay.

5. An inosculating device for inosculating alimentary canals according to claim 4, wherein: said handle is connected to said cylindrical body so as to form an angle of 90 degrees or more therebetween.

6. An inosculating device for inosculating alimentary canals according to claim 4 wherein: said top portion of said auxiliary appliance comprises a step disposed around an outer surface thereof, so that when said auxiliary appliance is inserted into the cylindrical body and protruding from said opening of the body, a smooth connection is obtained between the top portion and the opening of the cylindrical body.

7. An anal retractor system, comprising in combination:

a handle, having at least two grips and a slidable stay;

a plurality of plate-like members, each of which is curved to define a concave inner surface and a convex outer surface and arranged with respect to the other plate-like members to form a substantially circular opening; one of said plate-like members pivotally connected to a respective one of said grips, and another of said plate-like members coupled to said slidable stay, said handle operable to dilate said circular opening;

a device operably coupled to said handle for maintaining the dilated condition of said plate-like members;

a bullet-shaped auxiliary appliance configured to mount in said circular opening to protrude from a distal end of said plate-like members.

8. The anal retractor as defined in claim 7, wherein said handle is connected to said plate-like members at an angle of 90 degrees or more.

9. The anal retractor as defined in claim 7, wherein said bullet-shaped auxiliary appliance includes a step defined around an outer surface thereof to receive at least a portion of said distal end of said plate-like members.

10. The anal retractor as defined in claim 7, wherein said plate-like members define a tubular body when in a fully retracted condition.

11. The anal retractor as defined in claim 10, wherein said tubular body is cylindrical.

12. The anal retractor as defined in claim 7, wherein said device includes one of a latch mechanism and a gauge screw.

13. The anal retractor as defined in claim 7, further including an inosculator having an inserting portion.

14. The anal retractor as defined in claim 13, further including a clipping mechanism disposed at one end of said inserting portion.

15. The anal retractor as defined in claim 14, further including an operating portion disposed at an opposite end of said inserting portion, whereby damaged alimentary canals are inosculated with each other by inserting said inserting portion into said alimentary canals and operating said operating portion at said opposite end of said inserting portion.

16. A device for inosculating alimentary canals, comprising in combination:

a tubular body defined by at least three valve members, each having a generally concave inner surface and a generally convex outer surface;

a first and second handle grips, pivotally coupled to each other, and each having one end pivotally coupled to a respective one of said valve members;

a pin extending from one end of at least two of said valve members for pivotally coupling at least two valve members to said first and second handle grips, respectively; and a stay slidably coupled to said first and second handle grips and intermediate thereto, and having an end coupled to a third of said valve members.

17. The device for inosculating alimentary canals as defined in claim 16, further including:

an auxiliary appliance mounted to one end of said tubular body and configured to protrude therefrom;

an inosculator configured to extend through said tubular body and having an inserting portion defined at one end;

a clipping mechanism disposed at a distal end of said inserting portion; and an operating portion disposed at a proximal end of said inserting portion, whereby damaged alimentary canals are inosculated by inserting said inserting portion into said alimentary canals and operating said operating portion at a proximal end of said inserting portion.

18. The device for inosculating alimentary canals as defined in claim 17, wherein said tubular body defines a cylindrical body.

* * * * *

UNITED STATES PATENT AND TRADEMARK OFFICE
CERTIFICATE OF CORRECTION

PATENT NO.    :  5,681,265
DATED         :  October 28, 1997
INVENTORS     :  Koutarou Maeda et al.

It is certified that error appears in the above-identified patent and that said Letters Patent is hereby corrected as shown below:

Column 3, line 15;

"vales" should be --valves--.

Column 3, line 21;

"valve" should be --valves--.

Column 5, line 29;

"05b" should be --105b--.

Column 6, line 4;

After "parts" insert --other--.

Column 8, claim 1, line 23;

After "members" delete "is".

Column 10, claim 16, line 13;

"grips" should be --grip--.

UNITED STATES PATENT AND TRADEMARK OFFICE
CERTIFICATE OF CORRECTION

PATENT NO.  : 5,681,265
DATED       : October 28, 1997
INVENTORS   : Koutarou Maeda et al.

It is certified that error appears in the above-identified patent and that said Letters Patent is hereby corrected as shown below:

Column 10, claim 16, line 17;

Before "at least" insert --said--.

Signed and Sealed this

Tenth Day of March, 1998

Attest:

BRUCE LEHMAN

*Attesting Officer*      *Commissioner of Patents and Trademarks*